United States Patent [19]

Murakami

[11] 3,941,792

[45] Mar. 2, 1976

[54] CHARGE TRANSFER COMPLEXES CONTAINING 7,7,8,8-TETRACYANOQUINODIMETHANE AND AN N-SUBSTITUTED QUATERNARY QUINOLINE

[75] Inventor: Mutsuaki Murakami, Kawasaki, Japan

[73] Assignee: Matsushita Electric Industrial Co., Ltd., Kadoma, Japan

[22] Filed: June 7, 1973

[21] Appl. No.: 367,720

[30] Foreign Application Priority Data

June 8, 1972 Japan.............................. 47-57503

[52] U.S. Cl.......... 260/286 Q; 260/267; 260/279 R; 260/294.9; 260/315; 260/283 CN
[51] Int. Cl.².................................... C07D 215/10
[58] Field of Search................. 260/286 Q, 283 CN

[56] References Cited
UNITED STATES PATENTS

| 2,766,135 | 10/1956 | Middleton | 260/286 Q |
| 2,809,972 | 10/1957 | Middleton | 260/286 Q |
| 2,833,809 | 5/1958 | Middleton | 260/286 Q |
| 3,115,506 | 12/1963 | Acker et al. | 260/294.9 |
| 3,334,109 | 8/1967 | Harris | 260/283 CN |
| 3,681,353 | 8/1972 | Martin | 260/283 CN |

OTHER PUBLICATIONS

Melby, Can. J. of Chem., 43, 1448 (1965).

*Primary Examiner*—R. Gallagher
*Assistant Examiner*—David E. Wheeler

[57] ABSTRACT

Charge transfer complexes composed of 7,7,8,8-tetracyanoquinodimethane and a quaternary nitrogen-containing heterocyclic compound, the hydrogen at N-position of the heterocyclic compound being substituted by a group such as an alkyl group, an alkylene group or a cycloalkyle group. The complex may be either an abnormal one which contains neutral 7,7,8,8,-tetracyanoquinodimethane in an amount deviated from 1 mole per 1 mole of the complex, or a normal one which contains 1 mole of neutral 7,7,8,8-tetracyanoquinodimethane per 1 mole of the complex.

2 Claims, 4 Drawing Figures

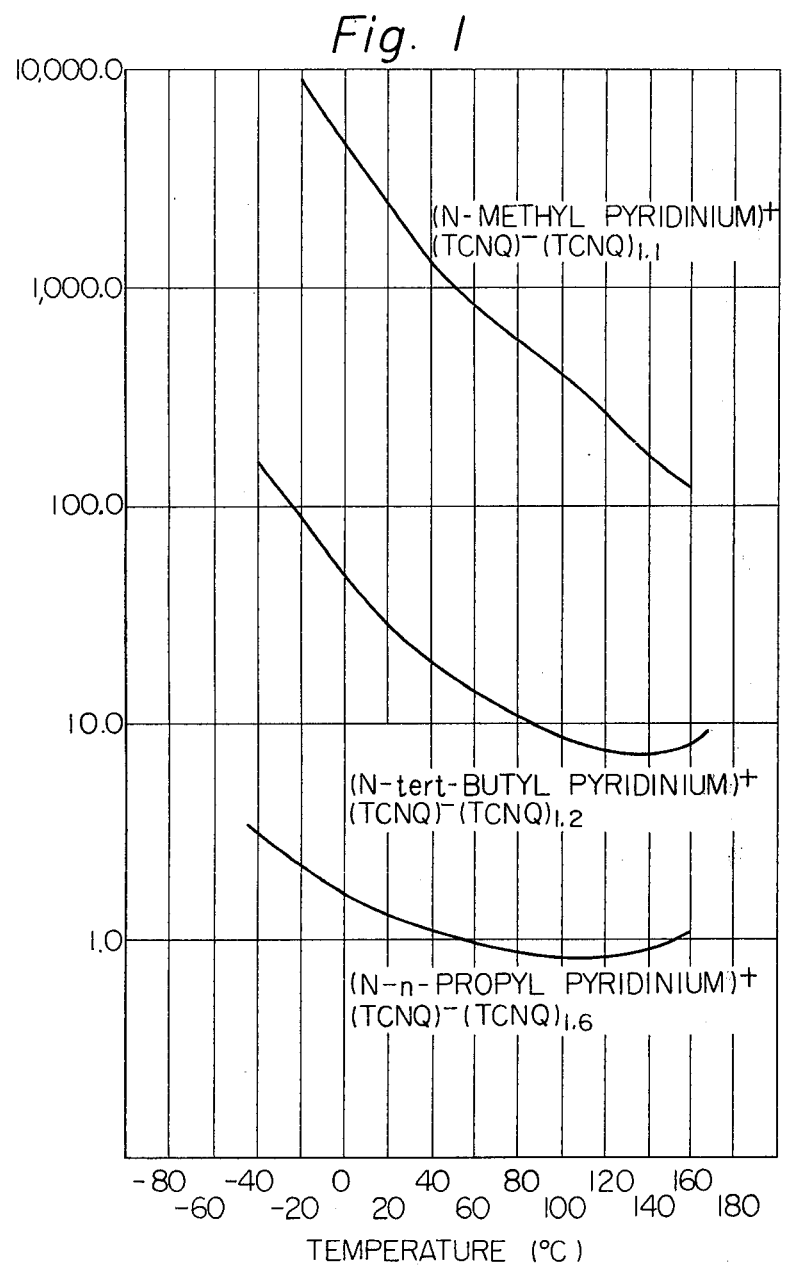

CHARGE TRANSFER COMPLEXES CONTAINING 7,7,8,8-TETRACYANOQUINODIMETHANE AND AN N-SUBSTITUTED QUATERNARY QUINOLINE

This invention relates to electric conductive materials and more particularly to charge transfer complexes composed of 7,7,8,8-tetracyanoquinodimethane and a N-substituted quaternary nitrogen-containing heterocyclic compound, hydrogen at N-position of the heterocyclic compound being substituted by a suitable organic group. 7,7,8,8-tetracyanoquinodimethane and a salt of 7,7,8,8-tetracyanoquinodimethane are hereinafter referred to simply as a TCNQ and TCNQ salt, respectively, for the sake of brevity.

In general, electric conduction of conductive materials is classified into two categories, one being metallic conduction wherein resistance of conductive materials increases with an increase of temperatures, and the other being semiconductive conduction wherein resistance of materials decreases with an increase of temperatures. Some organic semiconductive materials, particularly, having a low resistivity show metallic and semiconductive conductions at the same time in the vicinity of a normal temperature. Among organic semiconductive materials, TCNQ salts are well known in the art because of their low resistivity. TCNQ and its various salts and methods of preparation are described in Journal of American Chemistry Society 84, 3370 (1962) or Canadian Journal of Chemistry, 43, 1448 (1965), or in U.S. Pat. No. 3,115,506 or British Patent No. 882,138.

TCNQ salts include simple salts of TCNQ expressed by the following formula

wherein $M$ is a metallic or organic cation and $n$ is the valence of the cation and complex salts represented by a formula

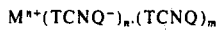

wherein M and $n$ have the same meanings as mentioned above and $m$ is a mole number of neutral TCNQ contained in one mole of the complex salt. The complex salts generally show a remarkably high conductivity and thus may be advantageously utilized as an organic resistor. Typical examples of the complex salts which have a high conductivity are those which have TCNQ as an anion and a nitrogen-containing aromatic onium salt, as a cation, having a pyridinium ring, a quinolinium ring or the like. In this instance, (pyridinium)$^+$(TCNQ)$^-$(TCNQ) complex salt has a specific resistance of 37ω-cm, and (quinolinium)$^+$(TCNQ)$^-$(TCNQ) a specific resistance of 0.4ω-cm. These organic semiconductive materials have, however, a disadvantage that they lack thermal stability, e.g., (quinolinium)$^+$(TCNQ)$^-$(TCNQ) and (pyridinium)$^+$(TCNQ)$^-$(TCNQ) lose their high conductivities at about 100°C and 110°C, respectively.

It is therefore an object of the present invention to provide an organic semiconductive material which overcomes the disadvantage of the prior-art organic semiconductive materials.

It is a further object of the invention to provide an organic semiconductive material which is thermally stable up to 150°C or more.

It is another object of the invention to provide an organic semiconductive material which has a relatively low resistivity.

It is another object of the invention to provide charge transfer complexes of TCNQ and a quaternary nitrogen-containing heterocyclic compound, the hydrogen at N-position of the heterocyclic compound being substituted by a suitable group.

It is still another object of the invention to provide charge transfer complexes containing therein netural TCNQ in an amount deviated from 1 mole per 1 mole of the complex.

The above objects are attained by charge transfer complexes composed of 7,7,8,8-tetracyanoquinodimethane and a quaternary nitrogen-containing heterocyclic compound, the hydrgoen at the N-position of the heterocyclic compound is substituted by an alkyl group, an alkylene group or a cycloaklyl group.

The invention will be better understood from the following description taken in conjunction with the accompanying drawings in which.

Figure 1:
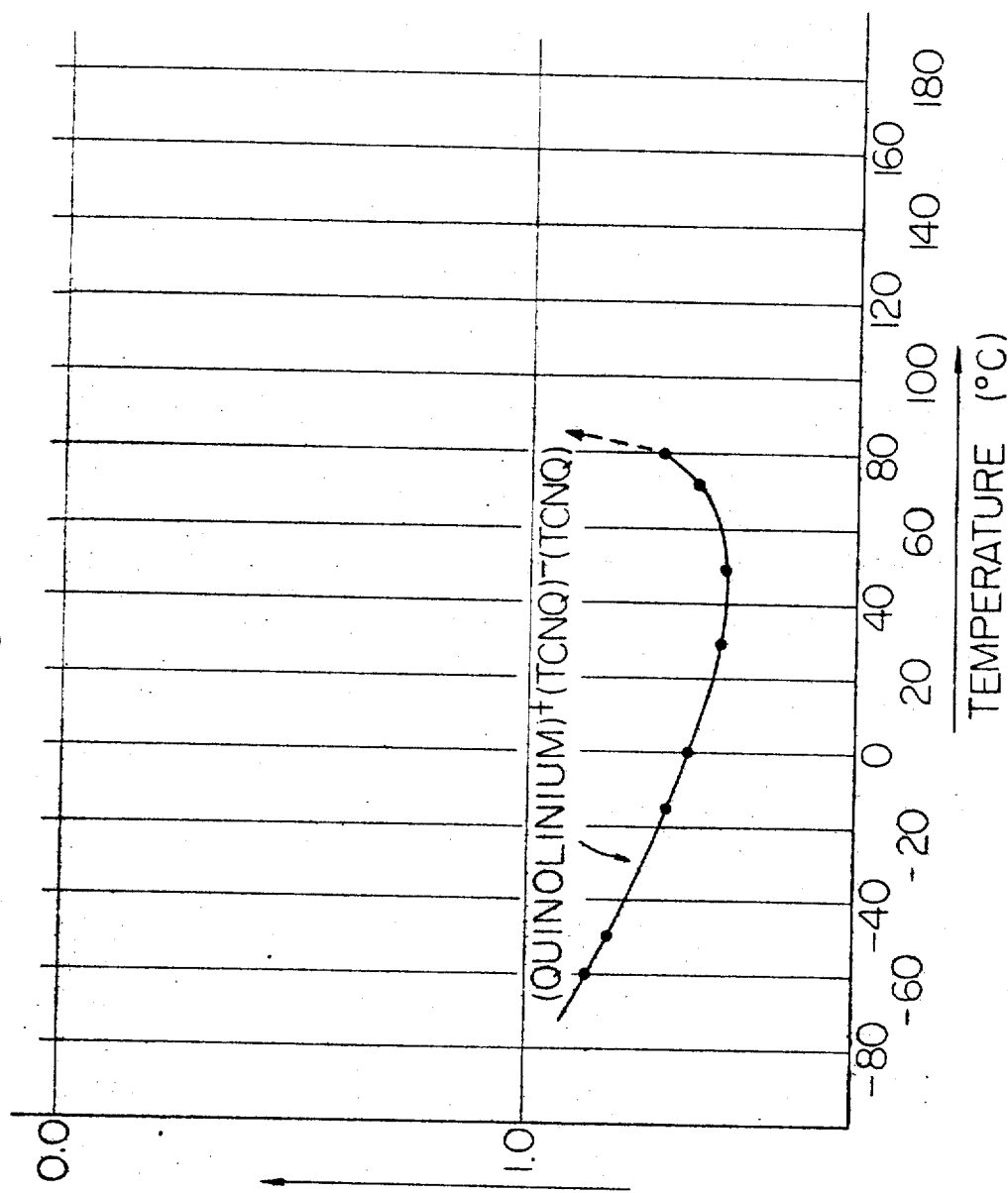
FIG. 1 is a curve illustrating the relation between resistivity and temperatures of a known charge transfer complex.
Figure 4:
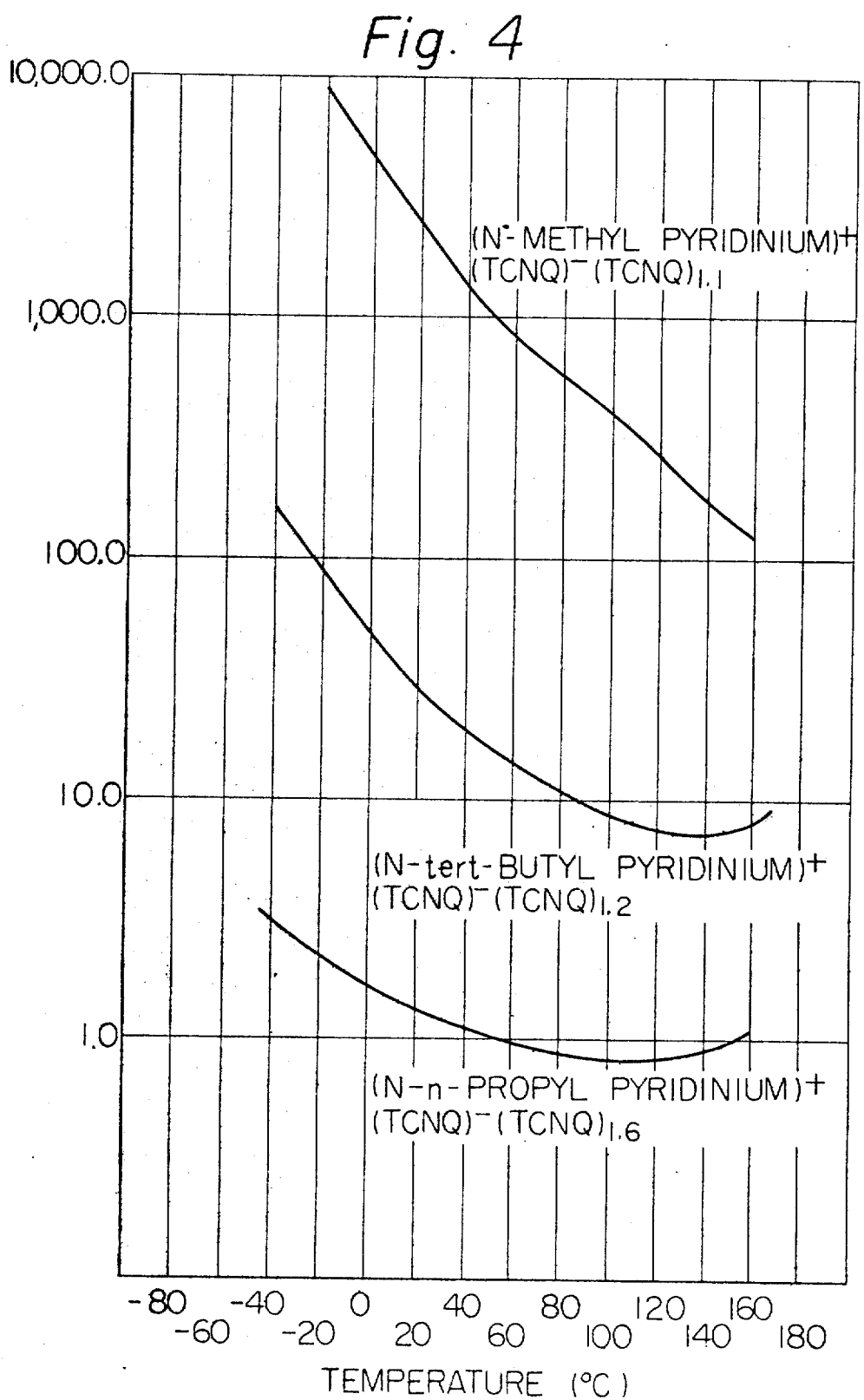

In order to grasp mechanisms of thermal stability of a known charge transfer complex, (quinolinium)$^+$(TCNQ)$^-$(TCNQ), the present inventor conducted a test wherein a resistivity of the complex was determined at different temperatures. This is shown in FIG. 1. When the complex was heated to a temperature higher than 80°C, a resistivity abruptly increased in an irreversible manner, as shown by a dotted line of FIG. 1. The temperature of 80° was taken as a thermally-stable point. Complex salt specimens before and after being thermally treated at a temperature beyond the thermally-stable point were subjected to tests including an elementary analysis, ultra-violet and visible light inspections etc., for investigating differences in structure between the complex salt specimens. Test results are summarized as follows:

1. The (quinolinium)$^+$(TCNQ)$^-$(TCNQ) complex salt almost completely loses its high electric conductivity when heated in the vicinity of 80°C.

2. An elementary analysis revealed that hydrogen of the complex salt which was treated at temperatures beyond a thermally-stable point decreased in amount.

3. When a pressed sample of the complex salt was heated to 100°C – 120°C, yellow powder appeared on the surface thereof. The powder was determined as free TCNQ by an elementary analysis.

4. Even when the resistivity of the complex salt was measured by a 4-probe method (wherein the reaction of the complex salt with electrodes could be satisfactorily avoided), the resistivity also deteriorated in the vicinity of 80°C.

From the above test results, it will be assumed that the deterioration in resistivity occurs in a manner as follows: the hydrogen atom at N-position of the quinolinium salt is released by thermal decomposition, and free TCNQ is separated from the complex salt, thus resulting in degradation in resistivity. That is, the deterioration in resistivity of the charge transfer complex is caused from thermal decomposition of the complex, followed by releasing hydrogen atom at N-position of the quaternary quinolinium salt.

On the basis of the above test results, the present inventors further conducted intensive studies on TCNQ-base complex salts and found that when the hydrogen at the N-position is replace by a suitable group, the thermal decomposition of the quaternary salt can be well prevented, thus preventing undesirable irreversible change in resistivity of the complex salt at least up to 150°C.

According to the present invention, there is provided charge transfer complexes composed of 7,7,8,8-tetracyanoquinodimethane and a quaternary nitrogen-containing heterocyclic compound, the hydrogen at N-position of the heterocyclic compound being substituted by an alkyl group, an alkylene group or a cycloalkyl group.

The alkyl group useful in the present invention contains from 1 to 18 carbon atoms, including methyl, ethyl, n-propyl, iso-propyl, n-butyl, tert-butyl, n-pentyl and its isomers, n-hyxyl and its isomers, n-heptyl and its isomers, n-octyl and its isomers, etc. The alkylene group contains from 2 to 12 carbon atoms, such as ethylene, propene, etc., and the cycloalkyl group from 5 to 8 carbon atoms, such as cyclopentyl, cyclohexyl, etc. Examples of the nitrogen-containing heterocyclic compounds include pyridine, quinoline, phenazine, acridine, carbazole, etc.

The charge transfer complex salts of the present invention may be a normal salt in which a mole number of free TCNQ contained in 1 mole of the complex salt is 1, or may be an abnormal salt wherein a mole number of free TCNQ contained 1 mole of the complex salt is deviated from 1. The abnormal salt is preferred because of its stable resistivity which hardly changes depending upon temperatures, when compared with a normal complex salt. Typical examples of the abnormal salts include (N-methyl quinolinium)$^+$(TCNQ)$^-$(TCNQ)$_{0.6}$,
(N-ethyl quinolinium)$^+$(TCNQ)$^-$(TCNQ)$_{0.8}$,
(N-n-propyl quinolinium)$^+$(TCNQ)$^-$(TCNQ)$_{0.9}$,
(N-iso-propyl quinolinium)$^+$(TCNQ)$^-$(TCNQ)$_{1.2}$,
(N-tert-butyl quinolinium)$^+$(TCNQ)$^-$(TCNQ)$_{2.1}$,
(N-methyl pyridinium)$^+$(TCNQ)$^-$(TCNQ)$_{1.1}$,
(N-ethyl pyridinium)$^+$(TCNQ)$^-$(TCNQ)$_{0.9}$,
(N-n-propyl pyridinium)$^+$(TCNQ)$^-$TCNQ)$_{1.6}$,
(N-tert-butyl pyridinium)$^+$(TCNQ)$^-$(TCNQ)$_{1.2}$, etc.

The complex salts of the present invention can readily be prepared by reacting iodized N-substituent and nitrogen-containing heterocyclic compound with TCNQ in a solvent, and allowing the reaction solution to stand for forming a crystal of a charge transfer complex salt. By suitably selecting a solvent and a molar ratio of TCNQ and the heterocyclic compound, either a normal salt or an abnormal salt may be obtained. For example, if dichloromethane is used as a solvent, a normal salt can be obtained, whereas if acetonitrile is used, an abnormal salt can be obtained. This will particularly be described in detail in the following Examples.

EXAMPLE 1

15 millimoles (3.0 g) of TCNQ were dissolved in 1300 ml of dichloromethane under reflux. Then, 7.5 millimoles (2.0 g) of iodized N-ethylquinolinium which were dissolved in 200 ml of dichloromethane were added to the TCNQ solution. The resultant solution was allowed to stand for several hours at room temperature thereby to obtain crystal. The thus obtained crystal was filtered and then was washed several times on the filter with dichloromethane until the filtrate turned to green. The thus washed crystal was further washed with ethyl ether until the filtrate turned colorless, to obtain (N-ethyl quinolinium)$^+$(TCNQ)$^-$(TCNQ).

Then, the thus obtained complex salt was powdered and the powdered salt was molded to form a rod having a diameter of 3 mm and a length of 15 mm. The rod was subjected to tests for determining a resistivity at 25°C and thermal stability thereof by a 4-probe method using Ag-paste electrodes.

The above process and tests were repeated except that several kinds of other iodized N-alkylquinolinium were used instead of the iodized N-ethylquinolinium.

The charge transfer complexes thus obtained were normal salts which contained 1 mole of neutral TCNQ in 1 mole of the charge transfer complex salt.

Test results are shown in Table 1 below, wherein a resistivity and thermal stability of known (quinolinium)$^+$(TCNQ)$^-$(TCNQ) are also shown for comparative purpose.

Table 1

| N-substituent | Resistivity $\rho(\Omega \cdot cm)$ | Thermally-Stable Point |
|---|---|---|
| Hydrogen | 0.4 | 100°C |
| Methyl | 2000.0 | 150°C |
| Ethyl | 16.1 | do. |
| n-propyl | 3.0 | do. |
| iso-propyl | 1.4 | do. |
| tert-butyl | 0.4 | do. |

Figure 2:
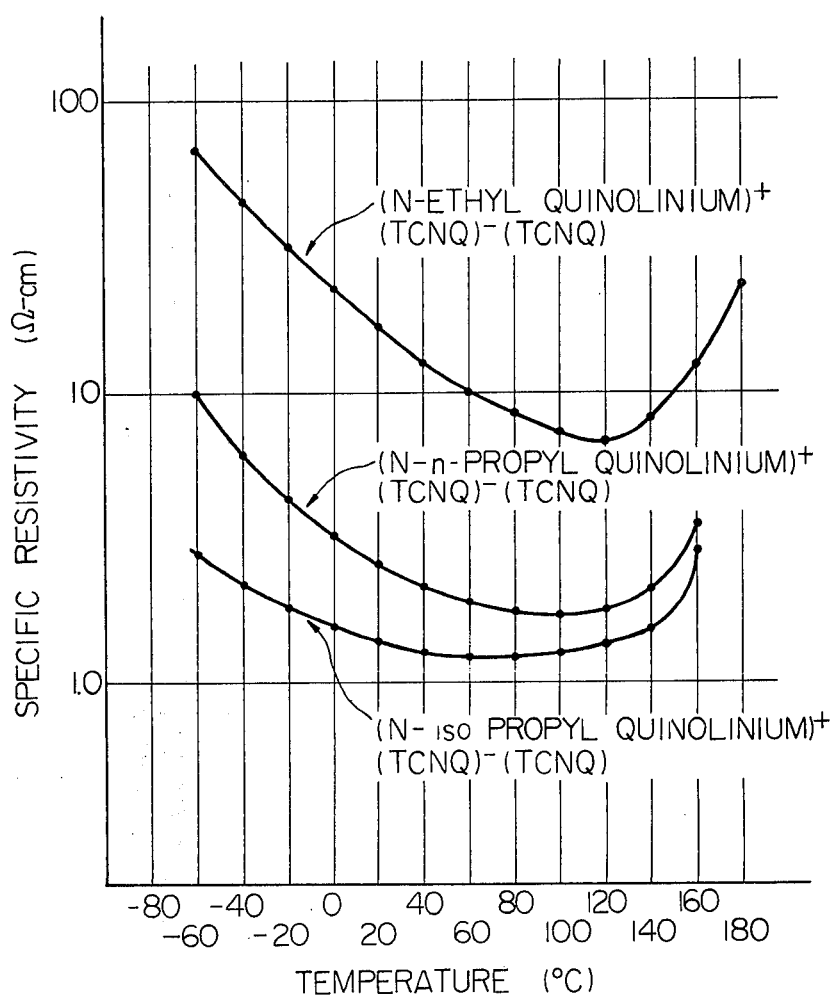
FIGS. 2, 3 and 4 are curves similar to that of FIG. 1 for charge transfer complexes of the invention.

Furthermore, there are shown in FIG. 2 curves illustrating a relation between resistivity and temperatures for (N-ethylquinolinium)$^+$(TCNQ)$^-$(TCNQ), (N-n-propylquinolinium)$^+$(TCNQ)$^-$(TCNQ), and (N-iso-Propyquinolinium)$^+$(TCNQ)$^-$(TCNQ).

As is apparent from the Table and FIG. 2, the (N-alkylquinolinium)$^+$(TCNQ)$^-$(TCNQ) is superior in thermal stability to known (quinolinium)$^+$(TCNQ)$^-$(TCNQ). The resistivity of the (N-alkylated quinolinium)$^+$(TCNQ)$^-$(TCNQ) tends to decrease with an increase in number of carbon atoms of the alkyl group.

EXAMPLE 2

Example 1 was repeated except that acetonitrile was used as a solvent.

Test results are shown in Table 2 below.

| N-substituent | Mole number of neutral TCNQ contained in 1 mole of Complex Salt | Resistivity $\rho(\Omega \cdot cm)$ | Thermally Stable Point |
|---|---|---|---|
| Hydrogen | 1 | 0.4 | 100°C |
| Methyl | 0.6 | 3000.0 | 150°C |
| Ethyl | 0.8 | 30.0 | do. |
| n-propyl | 0.9 | 3.2 | do. |
| iso-propyl | 1.2 | 0.7 | do. |
| Tert-butyl | 2.1 | 0.4 | do. |

Figure 3:
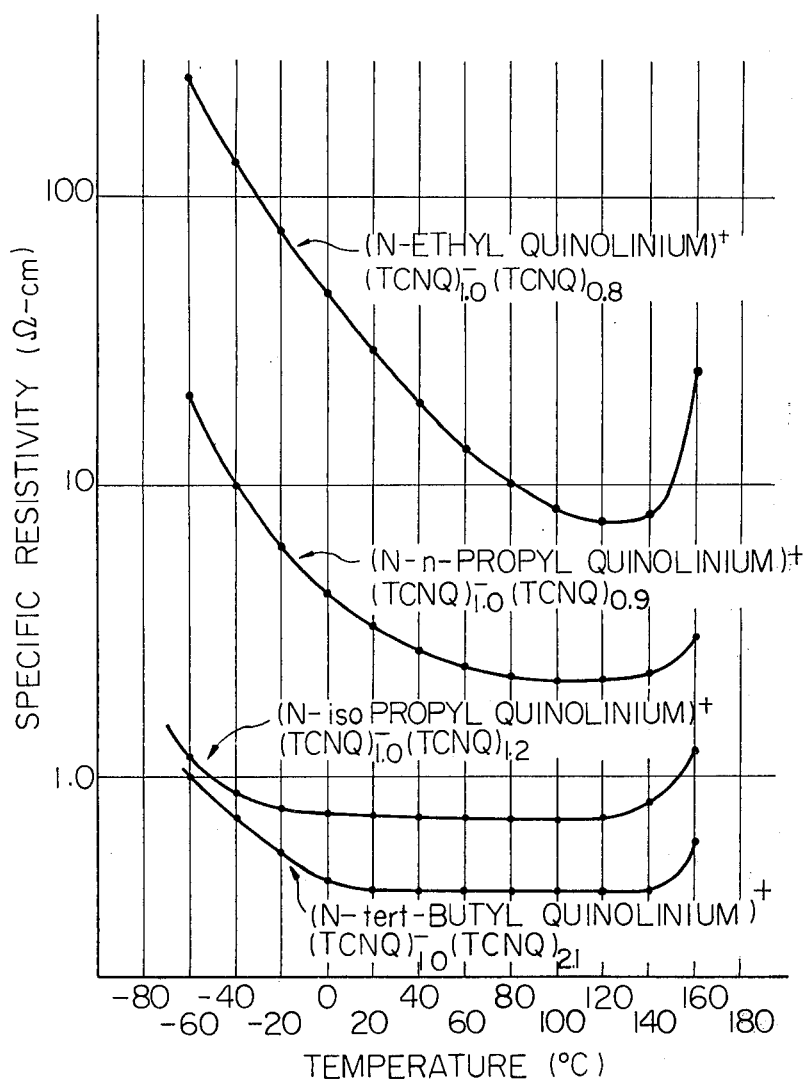

As is apparent from Table 2, when acetonitrile is used as a solvent, a mole number, $m$, of neutral TCNQ which is contained per 1 mole of (N-alkylquinolinium)(TCNQ)$^-$(TCNQ)$_m$ varies depending upon the kinds of the alkyl groups used. The mole number increases with an increase in number of carbon atoms of the alkyl group. All the N-substituted alkyl quinolinium and TCNQ abnormal complex salts have remarkably improved thermal stability. Moreover, the resistivity of the abnormal salts except for the methyl-substituted salt is maintained almost constant over a wide temperature range. This is apparently shown in FIG. 3. In particular, both (N-iso-propyl-quinolinium)$^+$(TCNQ)$^-$(TCNQ)$_{1.2}$ and (N-tert-butylquinolinium)$^+$(TCNQ)$^-$(TCNQ)$_{2.1}$ complex salts are satisfactorily small in resistivity which hardly varies depending upon temperatures, e.g., the former has small and almost constant resistivity over a temperature of 0°C to 130°C and the latter over a temperature of 20°C to 140°C, thus both being considered excellent as electric conductive materials.

EXAMPLE 3

Example 1 was repeated except that several kinds of iodized N-alkyl pyridium were used instead of N-ethyl-quinolinium and acetonitrile was used as a solvent, thereby to obtain (N-alkyl pyridinium)$^+$(TCNQ)$^-$(TCNQ)$_m$ wherein $m$ has the same meaning as indicated hereinbefore. The thus obtained (N-alkyl-pyridinium)$^+$(TCNQ)$^-$(TCNQ)$_m$ was subjected to tests for determining resistivity and thermal stability. For comparison, (pyridinium)$^+$(TCNQ)$^-$(TCNQ)$_{1.2}$ was also subjected to the same tests. Test results are shown in Table 3 below.

Table 3

| N-substituent | Moles of neutral TCNQ contained per 1 mole of Complex Salt | Resistivity $\rho(\Omega \cdot cm)$ | Thermally-Stable Point |
|---|---|---|---|
| Hydrogen | 1.2 | 37 | 110°C |
| Methyl | 1.1 | 2600 | 160°C |
| Ethyl | 0.9 | 2900 | do. |
| n-propyl | 1.0 | 2300 | do. |
|  | 1.6 | 200 | 150°C |
| iso-propyl | 1.0 | 41 | do. |

Table 3-continued

| N-substituent | Moles of neutral TCNQ contained per 1 mole of Complex Salt | Resistivity $\rho(\Omega \cdot cm)$ | Thermally-Stable Point |
|---|---|---|---|
| tert-butyl | 1.2 | 35 | do. |

Figure 4:
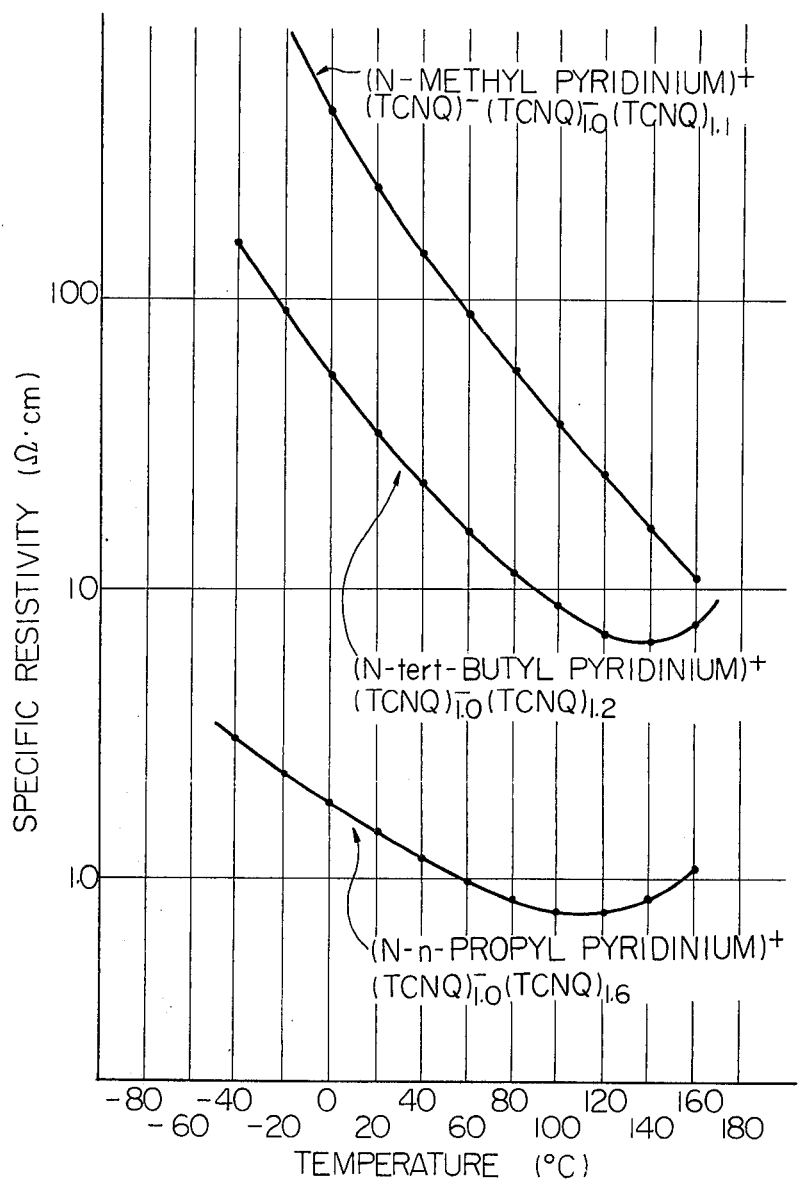

Since acetonitrile was used as a solvent, abnormal complex salts were also obtained in the same as in Example 2. With (N-propyl pyridinium)$^+$(TCNQ)$^-$(TCNQ)$_m$, there were obtained two kinds of crystals containing different molar amounts of neutral (TCNQ), i.e., $m = 1.0$ and 1.6, respectively. All of the N-substituted alkylpyridium-TCNQ complex salts were thermally stable at least up to 150°C. A relation between resistivity and temperatures N-alkylpyridium and TCNQ complex salts is shown in FIG. 4.

From the above description, it is seen that charge transfer complexes which contain TCNQ and a nitrogen-containing heterocyclic compound having N-substituted alkyl, alkylene or a cycloalkyl group are excellent in resistivity and thermal stability. Additionally, the resistivity of the complexes is reversible changed at least up to 150°C, e.g., the complex is thermally stable below the temperature.

It will be understood that numerous modifications and variations may be made by those skilled in the art without departing from the scope of the invention. Therefore, the appended claims are intended to cover all such equivalent variations as come within true spirit and scope of the invention.

What is claimed is:

1. A charge transfer complex of 7,7,8,8-tetracyanoquinodimethane (TCNQ) and an N-alkylated quinoline, the alkyl group having 1 to 18 carbon atoms, the complex comprising both ionized TCNQ molecules and non-ionized molecules, the mole number of the non-ionized TCNQ molecules per mole of the complex being other than one.

2. A charge transfer complex as claimed in claim 1 wherein said complex is one selected from the group consisting of (N-methyl quinolinium)$^+$(TCNQ)$^-$(TCNQ)$_{0.6}$, (N-ethyl quinolinium)$^+$(TNCQ)$^-$(TNCQ)$_{0.8}$, (N-n-propyl quinolinium)$^+$(TNCQ)$^-$(TNCQ)$_{0.9}$, (N-isopropyl quinolinium)$^+$(TCNQ)$^-$(TNCQ)$_{1.2}$, and (N-tert-butyl quinolinium)$^+$(TCNQ)$^-$(TNCQ)$_{2.1}$.

* * * * *

UNITED STATES PATENT AND TRADEMARK OFFICE
CERTIFICATE OF CORRECTION

PATENT NO. : 3,941,792

DATED : March 2, 1976

INVENTOR(S) : Mutsuaki Murakami

It is certified that error appears in the above-identified patent and that said Letters Patent are hereby corrected as shown below:

In the drawings of the above patent please cancel Figures 1 and 4 and substitute therefore Figures 1 and 4 as attached.

Signed and Sealed this

Fourteenth Day of September 1976

[SEAL]

Attest:

RUTH C. MASON
*Attesting Officer*

C. MARSHALL DANN
*Commissioner of Patents and Trademarks*